(12) United States Patent
Nikiforov et al.

(10) Patent No.: US 7,060,171 B1
(45) Date of Patent: Jun. 13, 2006

(54) METHODS AND SYSTEMS FOR REDUCING BACKGROUND SIGNAL IN ASSAYS

(75) Inventors: Theo T. Nikiforov, San Jose, CA (US); Aileen Zhou, San Leandro, CA (US)

(73) Assignee: Caliper Life Sciences, Inc., Mountain View, CA (US)

( * ) Notice: Subject to any disclaimer, the term of this patent is extended or adjusted under 35 U.S.C. 154(b) by 536 days.

(21) Appl. No.: 10/202,487

(22) Filed: Jul. 24, 2002

Related U.S. Application Data (60) Provisional application No. 60/309,113, filed on Jul. 31, 2001.

(51) Int. Cl.
*G01N 27/447* (2006.01)

(52) U.S. Cl. .................. 204/452; 204/451; 204/454

(58) Field of Classification Search ........ 204/601–603, 204/605, 451–455
See application file for complete search history.

(56) References Cited

U.S. PATENT DOCUMENTS

| | | | |
|---|---|---|---|
| 4,390,403 A | 6/1983 | Batchelder | |
| 4,908,112 A | 3/1990 | Pace | |
| 5,126,022 A | 6/1992 | Soane et al. | |
| 5,320,730 A * | 6/1994 | Ewing et al. | ............... 204/603 |
| 5,498,392 A | 3/1996 | Wilding et al. | |
| 5,571,410 A | 11/1996 | Swedberg et al. | |
| 5,585,069 A | 12/1996 | Zanzucchi et al. | |
| 5,593,838 A | 1/1997 | Zanzucchi et al. | |
| 5,603,351 A | 2/1997 | Cherukuri et al. | |
| 5,635,358 A | 6/1997 | Wilding et al. | |
| 5,637,469 A | 6/1997 | Wilding et al. | |
| 5,699,157 A | 12/1997 | Parce | |
| 5,716,852 A | 2/1998 | Yager et al. | |
| 5,750,015 A | 5/1998 | Soane et al. | |
| 5,800,690 A | 9/1998 | Chow et al. | |
| 5,858,187 A | 1/1999 | Ramsey et al. | |
| 5,858,195 A | 1/1999 | Ramsey | |
| 5,869,004 A | 2/1999 | Parce et al. | |
| 5,876,675 A | 3/1999 | Kennedy | |
| 5,880,071 A | 3/1999 | Parce et al. | |
| 5,882,465 A | 3/1999 | McReynolds | |
| 5,885,470 A | 3/1999 | Parce et al. | |

(Continued)

FOREIGN PATENT DOCUMENTS

WO     WO-9604547     2/1996

(Continued)

OTHER PUBLICATIONS

CAPLUS abstract of Sasamoto et al. ("Highly sensitive immunological assays for human chorionic gonadotropin and prostatic acid phosphatase using phenacyl phophate as a chemiluminescent label," Analytica Chimica Acta (1995), 309(1-3), 221-5).*

(Continued)

*Primary Examiner*—Alex Noguerola
(74) *Attorney, Agent, or Firm*—Donald R. McKenna; Ann C. Petersen (57) ABSTRACT

Methods and systems of monitoring reactions, e.g., assays, that filter out background signal from substrate, in detecting the product. The methods and systems controllably move detectable reaction product from a first location to a second location at which the product is detected while controllably moving potentially interfering substrate materials away from or not toward the second location. Controllable movement of the different species is accomplished through the controlled combination of bulk fluid flow and differential electrophoresis of substrate and product to move the product, but not the substrate past the detection region.

13 Claims, 6 Drawing Sheets

U.S. PATENT DOCUMENTS

| | | | |
|---|---|---|---|
| 5,932,100 | A | 8/1999 | Yager et al. |
| 5,942,443 | A | 8/1999 | Parce et al. |
| 5,948,227 | A | 9/1999 | Dubrow |
| 5,948,231 | A * | 9/1999 | Fuchs et al. ................ 204/601 |
| 5,955,028 | A | 9/1999 | Chow |
| 5,958,694 | A | 9/1999 | Nikiforov |
| 5,959,291 | A | 9/1999 | Jensen |
| 5,965,410 | A | 10/1999 | Chow et al. |
| 5,976,336 | A | 11/1999 | Dubrow et al. |
| 5,989,402 | A | 11/1999 | Chow et al. |
| 6,001,229 | A | 12/1999 | Ramsey |
| 6,001,231 | A | 12/1999 | Kopf-Sill |
| 6,012,902 | A | 1/2000 | Parce |
| 6,042,709 | A | 3/2000 | Parce et al. |
| 6,046,056 | A | 4/2000 | Parce et al. |
| 6,062,261 | A | 5/2000 | Jacobson et al. |
| 6,074,725 | A | 6/2000 | Kennedy |
| 6,100,541 | A | 8/2000 | Nagle et al. |
| 6,120,666 | A | 9/2000 | Jacobson et al. |
| 6,184,029 | B1 * | 2/2001 | Wilding et al. .......... 435/287.1 |
| 6,221,226 | B1 | 4/2001 | Kopf-Sill |
| 6,235,471 | B1 | 5/2001 | Knapp et al. |
| 6,280,589 | B1 | 8/2001 | Manz et al. |
| 6,306,273 | B1 * | 10/2001 | Wainright et al. .......... 204/454 |
| 6,627,406 | B1 * | 9/2003 | Singh et al. ................. 435/7.1 |
| 2002/0008029 | A1 | 1/2002 | Williams et al. |

FOREIGN PATENT DOCUMENTS

| | | |
|---|---|---|
| WO | WO-9702357 | 1/1997 |
| WO | WO 98/32010 A1 * | 7/1998 |
| WO | WO-0163270 | 8/2001 |

OTHER PUBLICATIONS

CAPLUS abstract of Kousaka et al. ("Evaluation of serum LH, FSH, E2, PRL, and hcg determination kit using automated enzyme immunoassay system AIA-1200XL," Igaku to Yakugaku (1994), 32(2), 355-64).*

CAPLUS abstract of Kitamura et al. ("A new highly sensitive chemiluminescent assay of alkaline phosphatase using lucigenin and its application to enzyme immunoassay," Journal of Bioluminescence and Chemiluminescence (1995), 10(1), 1-7).*

Dasgupta, P.K. et al., "Electroosmosis: A Reliable Fluid Propulsion System for Flow Injection Analysis," *Anal. Chem.* (1994) 66:1792-1798.

Effenhauser, C.S. et al., "Glass Chips for High-Speed Capillary Electrophoresis Separations with Submicrometer Plate Heights," *Anal. Chem.* (1993) 65: 2637-2642.

Effenhauser, C.S. et al., "High Speed Separation of Anitsense Oligonucleotides on a Micromachined Capillary Electrophoresis Device," *Anal. Chem.* (1994) 66: 2949-2953.

Effenhauser, C.S. et al., "Integrated Capillary Electrophoresis on Flexible Silicone Microdevices: Analysis of DNA Restriction Fragments and Detection of Single DNA Molecules on Microchips," *Anal. Chem.* (1997) 69: 3451-3457.

Fan, Z.H. et al., "Micromachining of Capillary Electrophoresis Injectors and Separators on Glass Chips and Evluation of Flow at Capillary Intersections," *Anal. Chem.* (1994) 66: 177-184.

Fister, J.C. III et al., "Counting Single Chromophore Molecules for Ultrasensitive Analysis and Separations on Microchip Devices," *Anal. Chem.* (1998) 70: 431-437.

Hadd, A.G. et al., "Microfluidic Assays of Acetylcholinesterase," *Anal. Chem.* (1999) 71: 5206-5212.

Harrison, J. et al., "Capillary Electrophoresis and Sample Injection Systems Integrated on a Planar Glass Chip," *Anal. Chem.* (1992) 64: 1926-1932.

Harrison, J. et al., "Towards Miniaturized Electrophoresis and Chemical Analysis Systems on Silicon: An Alternative to Chemical Sensors*," *Sensors and Actuators B* (1993) 10: 107-116.

Harrison, J. et al., "Micromachining a Miniaturized Capillary Electrophoresis-Based Chemical Analysis System on a Chip," *Science* (1993) 261: 895-897.

Harrison, D.J. et al., "Integrated Electrophoresis Systems for Biochemical Analyses," *Solid-State Sensor and Actuator Workshop* (1994) 21-24.

Jacobson, S.C. et al., "Effects of Injection Schemes and Column Geometry on the Performance of Microchip Electrophoresis Devices," *Anal. Chem.* (1994) 66:1107-1113.

Jacobson, S.C. et al., "High-Speed Separations on a Microchip," *Anal. Chem.* (1994) 66: 1114-1118.

Jacobson, S.C. et al., "Open Channel Electrochromatography on a Microchip," *Anal. Chem.* (1994) 66: 2369-2373.

Jacobson, S.C. et al., "Precolumn Reactions with Electrophoretic Analysis Integrated on a Microchip," *Anal. Chem.* (1994) 66: 4127-4132.

Jacobson, S.C. et al., "Microchip Electrophoresis with Sample Stacking," *Electrophoresis* (1995) 16: 481-486.

Jacobson, S.C. et al., "Fused Quartz Substrates for Microchip Electrophoresis," *Anal. Chem.* (1995) 67: 2059-2063.

Jacobson, S.C. et al., "Integrated Microdevice for DNA Restriction Fragment Analysis," *Anal. Chem.* (1996) 68: 720-723.

Jacobson, S.C. et al., "Electrokinetic Focusing in Microfabricated Channel Structures," *Anal. Chem.* (1997) 69: 3212-3217.

Jacobson, S.C. et al., "Microfluidic Devices for Electrokinetically Driven Parallel and Serial Mixing," *Anal. Chem.* (1999) 71: 4455-4459.

Manz, A. et al., "Miniaturized Total Chemical Analysis Systems: a Novel Concept for Chemical Sensing," *Sensors and Actuators* (1990) B1: 244-248.

Manz, A. et al., "Micromachining of Monocrystalline Silicon and Glass for Chemical Analysis Systems," *Trends in Analytical Chemistry* (1991) 10:144-149.

Manz, A. et al., "Planar Chips Technology for Miniaturization and Integration of Separation Techniques into Monitoring Systems," *Journal of Chromatography* (1992) 593:253-258.

Manz, A. et al., "Planar Chips Technology for Miniaturization of Separation Systems: A Developing Perspective in Chemical Monitoring."

Manz, A. et al., "Electroosmotic Pumping and Electrophoretic Separations for Miniaturized Chemical Analysis Systems," *J. Micromach. Microeng.* (1994) 4: 257-265.

Manz, A. et al., "Parallel Capillaries for High Throughput in Electrophoretic Separations and Electroosmotic Drug Discovery Systems," International Conference on Solid-State Sensors and Actuators (1997) 915-918.

McCormick, R.M. et al., "Microchannel Electrophoretic Separations of DNA in Injection-Molded Plastic Substrates," *Anal. Chem.* (1997) 69: 2626-2630.

Moore, A.W. et al., "Microchip Separations of Neutral Species via Micellar Electrokinetic Capillary Chromatography," *Anal. Chem.* (1995) 67: 4184-4189.

Ramsey, J.M. et al., "Microfabricated Chemical Measurement Systems," *Nature Medicine* (1995) 1:1093-1096.

Salimi-Moosavi, H. et al., "Biology Lab-on-a-Chip for Drug Screening," Solid-State Sensor and Actuator Workshop (1998) 350-353.

Seiler, K. et al., "Planar Glass Chips for Capillary Electrophoresis: Repetitive Sample Injection, Quantitation, and Separation Efficiency," *Anal. Chem.* (1993) 65:1481-1488.

Seiler, K. et al., "Electroosmotic Pumping and Valveless Control of Fluid Flow within a Manifold of Capillaries on a Glass Chip," *Anal. Chem.* (1994) 66:3485-3491.

Ueda, M. et al., "Imaging of a Band for DNA Fragment Migrating in Microchannel on Integrated Microchip," *Materials Science and Engineering C* (2000) 12:33-36.

Wang, C. et al., "Integration of Immobilized Trypsin Bead Beds for Protein Degestion within a Microfluidic Chip Incorporating Capillary Electrophoresis Separations and an Electrospray Mass Spectrometry Interface," *Rapid Commin. Mass Spectrom.* (2000) 14:1377-1383.

Woolley, A.T. et al., "Ultra-High-Speed DNA Fragment Separations Using Microfabricated Capillary Array Electrophoresis Chips," *Proc. Natl. Acad. Sci. USA* (1994) 91:11348-11352.

Woolley, A.T. et al., "Functional Integration of PCR Amplification and Capillary Electrophoresis in a Microfabricated DNA Analysis Device," Anal. Chem. (1996) 68: 4081-4086.

Woolley, A.T. et al., "High-Speed DNA Genotyping Using Microfabricated Capillary Array Electrophoresis Chips," *Anal. Chem.* (1997) 69:2181-2186.

Woolley, A.T. et al., "Capillary Electrophoresis Chips with Integrated Electrochemical Detection," *Anal. Chem.* (1998) 70:684-688.

Zhang, B. et al., "Microfabricated Devices for Capillary Electrophoresis-Electrospray Mass Spectrometry," *Anal. Chem.* (1999) 71:3258-3264.

Manz et al., Planar Chips Technology for Miniaturization of Separation Systems: A Developing Perspective in Chemical Monitoring, (1993) Adv. Chrom., 33:1-66.

* cited by examiner

METHODS AND SYSTEMS FOR REDUCING BACKGROUND SIGNAL IN ASSAYS

CROSS-REFERENCE TO RELATED APPLICATION

This application claims the benefit of U.S. Provisional Patent Application No. 60/309,113, filed Jul. 31, 2001, which is incorporated herein by reference in its entirety for all purposes.

BACKGROUND OF THE INVENTION

A number of advances have been made in the fields of biotechnology and pharmaceutical research to increase the speed and accuracy of analytical operations. In at least one major advancement, technologies developed for the semiconductor industry have been adapted to manufacture miniaturized integrated devices that can be used to perform analytical operations much more quickly, with much greater accuracy, and with less operator involvement. These microfluidic devices have been commercially adapted for genetic and protein analysis in the form of the Agilent 2100 Bioanalyzer and associated LabChip® microfluidic devices and reagents developed by Caliper Life Sciences, Inc. Other commercial applications for microfluidic devices and systems are in the pharmaceutical industry where they are used in ultra high-throughput screening analysis. These systems allow large numbers of different pharmaceutical candidate compounds to be screened against target assays in relatively short amounts of time, to determine whether any of those compounds possess desirable pharmacological activity. The resulting assays give improved data quality and increased automation, while minimizing the amounts of potentially very expensive reagents.

While microfluidic systems have been shown to improve the speed and accuracy of screening assays, there are a number of areas where the small size and enhanced speed of these systems can be a handicap to a screening assay. This is the case, for example, where a particular analyte is at a very low concentration in the fluid that is being tested. In such instances, the small volumes of the fluid that are present in a detection region of a microfluidic device may contain only a few hundred molecules of interest. In such cases, the amount of material present may fall below the detection level of the particular system that is being employed. Similarly, for assays that progress at relatively slow rates, the speed of operation of microfluidic systems may cause some difficulty in yielding enough product of the reaction so that it can be readily and accurately detected. The present invention provides some solutions for these problems, as well as others that may be faced in microfluidic and other analytical systems.

BRIEF SUMMARY OF THE INVENTION

The present invention generally provides methods of monitoring reactions, e.g., assays, that filter out background signal from substrate, in detecting the product. In a first aspect, the invention provides a method of monitoring a reaction that comprises providing a quantity of a first reaction mixture at a first location in a fluidic conduit. The first reaction mixture comprises a first reagent having a detectable label associated therewith, and a second reagent that reacts with the first reagent to produce a first product having the detectable label associated therewith, and an electrophoretic mobility that is different from the first reagent. A detection zone is provided at a second location in the first fluidic conduit, wherein the second location is different from the first location. An electric field is then applied to the first reaction mixture and bulk fluid flow through the fluid conduit is controlled, whereby under the applied electric field, the first product moves from the first location to the second location in a substantially greater ratio to the first reagent, as compared to the ratio of product to first reagent at the first location. The product is then detected at the second location.

In a related aspect, a method is provided for monitoring a reaction that comprises providing a fluid channel that comprises a first channel segment and a second channel segment. Reagents are introduced into the first channel segment that include a substrate for the reaction having a detectable label associated therewith and a first electrophoretic mobility, and a first reagent that reacts with the substrate to produce a first product that includes the detectable label and a second electrophoretic mobility that is different from the first electrophoretic mobility. An electric field is applied (initiated or maintained) between the first channel segment and the second channel segment and the bulk fluid flow is controlled between the first channel segment and the second channel segment, whereby the substrate, but not the product is substantially directed away from the second channel segment. The product is then detected in the second channel segment.

In yet another related aspect, the invention provides a method of monitoring a reaction that comprises providing a fluid conduit having first and second zones that are at different locations from each other. A quantity of a reaction mixture is provided in the first zone that includes a first reagent having a detectable label and a first electrophoretic velocity in the direction of the second zone of $V_S$ under an applied electric field, and a second reagent that reacts with the first reagent to produce a product that includes the detectable label and as a second electrophoretic velocity in the direction of the second zone of $V_P$ under the applied electric field. The electric field is applied across a length of the fluid conduit between the first and second zones and bulk fluid movement in the direction from the first zone to the second zone (F) is controlled, whereby $F+V_P$ is greater than 0 and $F+V_S$ is less than or equal to 0. Again, the product is detected at the second zone.

DETAILED DESCRIPTION OF THE INVENTION

I. General

The present invention is generally directed to methods of monitoring reactions, and particularly to assay methods that exploit changes in electrophoretic mobility of the product relative to the substrate in order to characterize the extent and/or speed of the reaction in questions. While shifts in electrophoretic mobility have been used to characterize reactions previously, the present invention utilizes a controlled bulk fluid flow, in conjunction with the shift in electrophoretic mobility to remove any, or at least a substantial amount of background substrate signal during the detection step in order to achieve higher sensitivity and accuracy.

Typically, assay formats that utilize shifts in electrophoretic mobility, also termed "mobility shift assays", involve a simple electrophoretic separation of the substrate and product after the reaction that alters the electrophoretic mobility of the product relative to the substrate, where both substrate and product are detected. As used herein, "electrophoretic mobility" refers to the net mobility of a chemical species when subjected to an electric field, which mobility is solely attributable to the charge based movement of that species under the electric field. Electrophoretic mobility is generally used as a relative term, in that changes in electrophoretic mobility of, e.g., a product relative to a substrate, generally denotes situations where conditions that might effect the electrophoretic mobility of the species that are external to the species, e.g., environmental conditions such as pH, and salt concentration, remain substantially unchanged.

Figure 1:
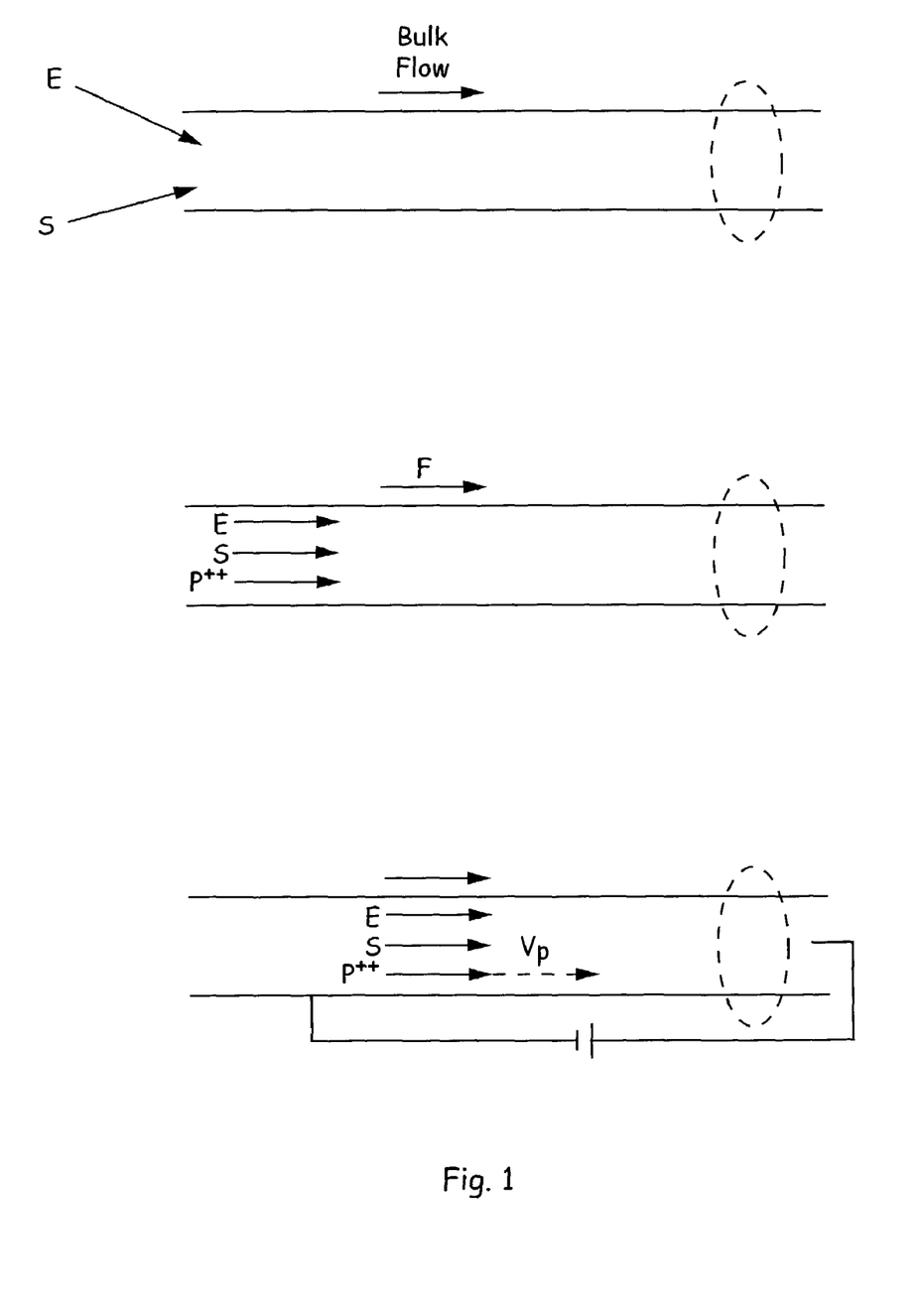
FIG. 1 is a schematic illustration of a conventional mobility shift assay method.

FIG. 1 schematically illustrates a typical mobility shift assay format as traditionally carried out in a capillary channel, i.e., a capillary or channel of a microfluidic device. As shown, an enzyme (E) and a labeled substrate (S) are introduced into a fluid conduit, e.g., a capillary or a channel in a fluidic device. The interaction of the substrate and the enzyme results in a product (P) that has changed in its electrophoretic mobility relative to the substrate, but still includes the detectable label from the substrate. Under a constant applied electric field (E), this shift in electrophoretic mobility ($\mu$) results in a shift in the electrophoretic velocity (V) of the product relative to the substrate. Briefly, the electrophoretic mobility of a compound is independent of the electric field applied, while the electrophoretic velocity is dependent upon the applied electric field, e.g., $V=(\mu)(E)$.

The shift in electrophoretic mobility, and consequently, electrophoretic velocity is typically caused by a change in the charge-to-: mass ratio of the product relative to the substrate. By way of example, an uncharged substrate may have a highly charged chemical group attached to it or removed from it by the action of the enzyme that is being assayed, e.g., a phosphate group attached by a kinase. In another example, a substrate may be acted upon by the enzyme in question to cleave or otherwise separate the substrate into two products. By providing a substrate with an uneven charge distribution, it can result in at least one product that has a substantially different charge-to-: mass ratio and thus, a substantially different electrophoretic mobility and velocity from the substrate. For example, a polypeptide can be provided with a highly charged region that is away from the cleavage zone for a protease of interest. Cleavage of the polypeptide then shifts the electrophoretic mobility of each product (e.g., both fragments) relative to the substrate polypeptide as a whole.

Referring again to FIG. 1, the reaction mixture is typically flowed along the conduit while the reaction is occurring, or after the reaction has occurred. This flow is typically as a result of the bulk flow of the fluid through the conduit (as indicated by the solid arrows), which results in equivalent flow of all of the components of the reaction mixture (E, S and P). While moving, the reaction mixture is subjected to an electric field, which then results in a differential electrophoretic velocity of the substrate and product (as indicated by the dashed arrow associated with the product). The whole mixture is flowed past the detection point (as indicated by the dashed ellipse). Because the product is moving at a different rate (the sum of the bulk flow and the electrophoretic velocity) from the substrate (moving with the bulk flow), it results in detection of one labeled species as the product and another that represents the substrate. Because separations are never perfect, there can be some overlap between these peaks, reducing the overall resolution of the assay format. In particular, any substrate that is detected at the same time as the product is detected results in a higher background level signal. Further, in order to assure more sensitive detection, one may need to perform the electrophoretic separation over a longer distance and for longer periods of time, in order to ensure adequate separation between the product and substrate.

The presence of substrate and product during the detection step is particularly problematic in continuous flow assay methods and systems, e.g., as described in U.S. Pat. Nos. 5,942,443 and 6,046,056, each of which is incorporated herein by reference in its entirety for all purposes. In these continuous flow assays, in a continuing stream of reaction components, e.g., enzyme and substrate, is flowed along the analysis channel or conduit, which react and produce a steady state amount of product by the time the mixture reaches a detection point. When a test compound that has an effect on the reaction, e.g., as an inhibitor, is introduced into the flowing stream, it produces a perturbation in the steady state amount of product. In typical fluorogenic assays, this perturbation is readily measured as a shift in the amount of detectable signal. In mobility shift assays, however, both the product and substrate have the same signal. As such, an electric field is applied to the mixture, resulting in localized concentration and depletion of substrate and product to yield a representative signal profile. For example, fluorescent product that moves faster under an electric field will move ahead of the slower moving substrate. In the absence of an inhibitor, this difference is undetectable, as the overall flowing is constant. When an inhibitor is introduced in a discrete plug into the flowing stream, it results in a reduction in the amount of product, yielding a consequent reduction in the amount of signal running ahead of the mixture. This also produces an increase in the amount of slower, unreacted substrate running with or behind the reaction mixture.

While these methods have proven effective, the existence of a constant stream of both substrate and product through the conduit results in a certain level of background fluorescence, from the omnipresent substrate. In particular, while the overall reaction produces an overall signal indicative of a perturbation in the amount of product produced, that signal is overlaid on a constant signal from a certain steady state level of substrate. This constant signal reduces the overall sensitivity level of the assay, e.g., the signal of interest, e.g., from the product, may be only a small fraction of the overall fluorescence emanating from the reaction mixture. This is complicated further in assay systems that have relatively slow reaction kinetics, e.g., enzymes with slow substrate turnover rates. In particular, the change in signal resulting from a perturbation in the amount of product produced, where very little product is produced, can be very small as compared to the background signal from substrate, and can be lost in the noise from the relatively high level of substrate signal. As such, these slower reactions can be very difficult to analyze.

By filtering out background levels of substrate from the detected product (and perturbations of the product) the methods of the present invention increase the sensitivity of the overall assay, and allow the assay method to be applied more readily to assays that have substantially slower kinetics. The present invention filters out the background signal emanating from substrate by directing the substrate away from the detection zone, while permitting the product to proceed through the detection zone. In general, this is accomplished by electrophoresing one of the substrate or the product in the desired direction. The differential flow direction of the other species may be the result of opposite electrophoretic velocity, or bulk fluid flow, or both.

Figure 2:
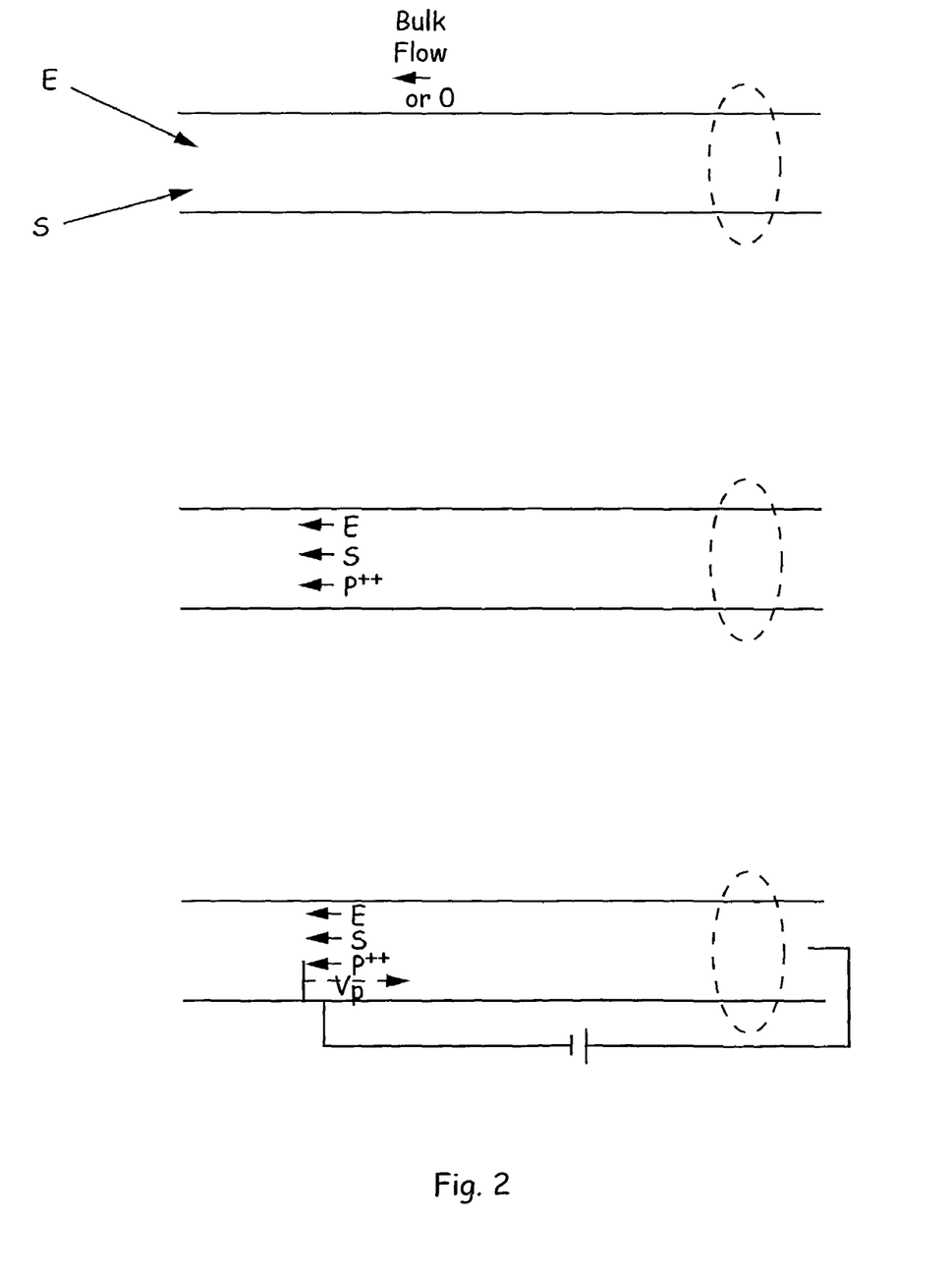
FIG. 2 is a schematic illustration of the mobility shift assay methods of the present invention that filter out background substrate signal from detected product.

An example of the methods of the present invention is schematically illustrated in FIG. 2, in a format similar to that of FIG. 1. In particular, as shown the enzyme E and substrate S are introduced into the conduit. In this instance however, a different bulk flow profile is used (as shown, bulk flow (F) is slightly away from the detection zone), as shown by the solid arrows. When the electric field is applied, the product still has a net overall flow in the direction of the detector, as shown by the combination of the solid and dashed arrows associated with the product (P), e.g., the sum of the electrophoretic velocity of the product ($V_P$) (a highly positive value) and the bulk flow (F) (slightly negative value) is greater than zero. Again, the substrate has an overall velocity that is the sum of the bulk flow and the electrophoretic velocity of the substrate ($V_S$) (which is shown as zero). In this instance, however, the bulk flow is in a direction away from the detector. Consequently, the substrate, which is moving with the bulk flow is also directed away from the detector, e.g., the sum of the electrophoretic velocity of the substrate toward the detector (zero, as shown) and the bulk flow toward the detector (shown as a negative value) is less than or equal to 0. As a result, only the product moves past the detector. This eliminates any background signal from the substrate that might reduce the sensitivity of the overall assay. While the benefits of the methods of the invention are clearest in small scale systems, e.g., microfluidics, where assay sensitivity is at a premium, the methods are also useful in enhancing the sensitivity of larger scale systems, e.g., non-microscale systems. Although described in terms of the bulk flow being in a direction away from the detector, it will be appreciated that bulk flow may be in the direction of the detector where the product flows with the bulk flow, provided that the substrate's overall mobility is away from the detection zone.

Although the above illustration is with respect to a substrate that has no electrophoretic mobility under the applied electric field, it will be appreciated that substrates that have electrophoretic mobility can be used in these methods, whether that mobility is in the same or in a different direction from the product, provided that the electrophoretic velocity of the substrate is sufficiently different from that of the product. For example, where the substrate has some electrophoretic velocity, e.g. in the direction of the detection zone, the bulk flow may be adjusted to be of sufficient magnitude to overcome that electrophoretic mobility, but not of sufficient magnitude to overcome the electrophoretic mobility of the product. Where, on the other hand, the substrate has an electrophoretic mobility in the direction opposite to that of the product, then no bulk flow may be required, and in fact, bulk flow toward the detection zone may be used to increase the speed at which the product reaches the detector, provided the bulk flow is not sufficient to overcome the electrophoretic mobility of the substrate in the opposite direction. Accordingly, the desired result is that the overall flow of the substrate toward the detection zone, e.g., the sum of electrophoretic velocity of the substrate ($V_S$) and bulk flow (F) is less than or equal to zero, while the overall flow of the product toward the detection zone, e.g., the sum of the electrophoretic velocity of the product ($V_P$) and the bulk flow (F) is greater than zero.

Although illustrated with respect to a single straight fluid conduit, it will be appreciated that the methods of the present invention are most useful in the context of integrated fluid channel networks, e.g., lab-on-chip devices. The methods of the invention are schematically illustrated in such an integrated device in FIG. 3A. As shown, the device 300 includes a main reaction channel 302 that is fluidly coupled to an external sampling capillary (not shown) via port 310, for sampling test compounds into the reaction channel 302. Reagent channels 304 and 306 are fluidly coupled to the main reaction channel 302, and bring in reagents for the assay, e.g., enzyme and substrate, respectively, from reservoirs 320 and 322. A detection channel 308 is provided fluidly connected to the main channel 302, and the product of the assay reaction is directed preferentially down this channel through detection zone 324 toward waste reservoir 326, while the substrate continues to flow along the reaction channel toward waste reservoir 330, or flows into optional auxiliary channel 312 toward reservoir 328, which may be employed, e.g., to allow application of an electric field that separates product and substrate, and directs product into the detection channel 308. Although illustrated with two reagent reservoirs 320 and 322, it will be appreciated that in certain preferred aspects, additional reservoirs and connecting channels may be provided for storing additional reagents and/or buffers and diluent for the reagent present in reservoirs 320 and 322.

Figure 3A:
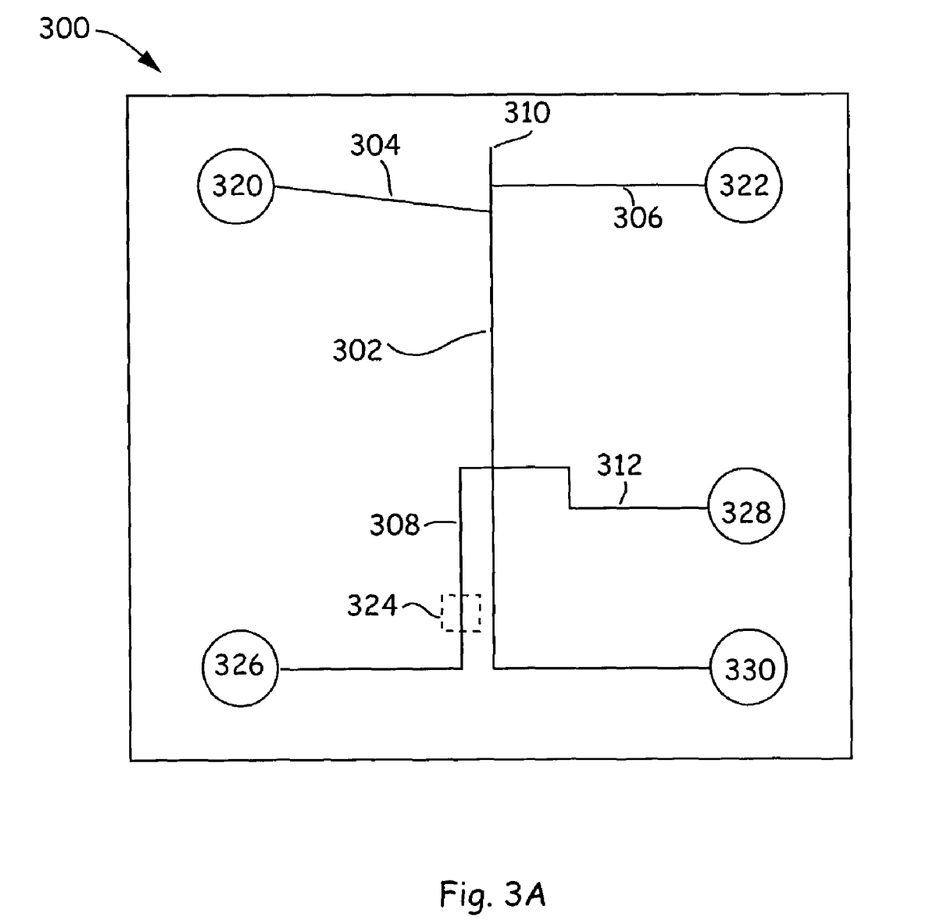
FIG. 3 is a schematic illustration of an integrated channel network approach to practicing the invention.
Figure 3B:
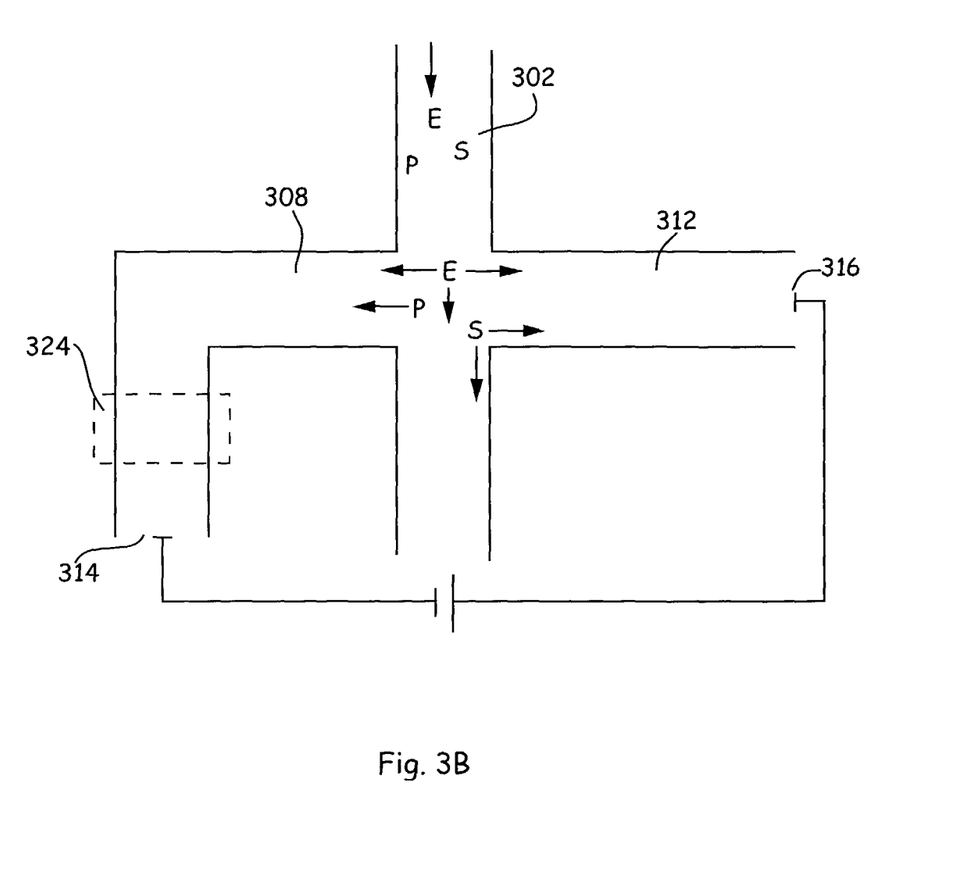

Operation of the device illustrated in FIG. 3A, in the methods of the invention, is schematically illustrated in FIG. 3B, which illustrates a close-up of the intersection region of channels 302, 308 and 312 during operation. As can be seen, the reaction mixture introduced into the main reaction channel includes an enzyme (E) and a substrates (S), which react to produce the product (P). The bulk flow of the reaction mixture is directed down the entire length of the main reaction channel 302. An electric field is applied through the intersection of the reaction channel and detection channel 308 and auxiliary channel 312, e.g., via electrodes 314 and 316, respectively. Because of its different electrophoretic velocity under the applied electric field (resulting from a shift in its electrophoretic mobility), the product is driven from the reaction channel 302 into the detection channel 308, by virtue of the applied electric field. The substrate is either carried on through the reaction channel by the bulk flow of the fluid, e.g., if the substrate is substantially uncharged, or directed into auxiliary channel 312, by the electric field, as indicated by the arrows, as a result of the combination of bulk flow and the electrophoretic velocity of the substrate being net away from the detection zone in the detection channel.

By controlling the bulk flow and the electric field, one can optimally direct the product into the detection channel, while only allowing only a small amount or no substrate into the detection channel. In preferred aspects, this is accomplished by forcing the substrate in a different direction from the product. However, it will be appreciated that by adjusting the bulk flow of fluid through the reaction channel, one can ensure that the substrate is not exposed to the electric field for sufficient time or does not have access to the entry to the detection channel for sufficient time to permit substantial amounts of substrate to be directed into the detection channel. This is slightly different from the net movement of substrate away from the detection zone, as described above, in that the substrate may have a net overall flow toward the detection zone, but that this net overall flow toward the detection zone is substantially reduced relative to the product. By thus reducing the opportunity for the substrate to move in the direction of the detection zone., e.g., by moving the substrate through an intersection with the detection channel at sufficient rate to minimize the entry of the substrate into the detection channel, one can substantially reduce the interfering substrate being detected.

As a result of the various methods of the invention, the ratio of product to substrate in the detection channel is increased substantially as compared to the ratio in the reaction channel. Typically, the methods of the invention will result in at least a 2 fold, preferably, at least a 5 fold, and often a 10, 100 or 500 fold increase in the ratio of product to substrate in the detection zone, as compared to that ratio within the reaction channel in the absence of the applied electric field. In preferred aspects, the labeled substrate is substantially directed away from the detection zone, e.g., by continuing to be directed along the reaction channel or by being directed into an auxiliary channel. By "substantially directed away" from the detection zone is meant that at least 50% of the labeled substrate is moved from the reaction channel or location, e.g., the first location, in a direction in the conduit or conduit network that is away from the detection zone, or second location. In preferred aspects, at least 90%, more preferably, at least 95% and in some cases, at least 99% of the labeled substrate is moved in a direction other than through a channel toward the detection zone.

As noted above, in the case where the product and substrate are each charged, e.g., each having a different net positive charge or net negative charge, then the bulk fluid flow within the reaction channel may be adjusted to optimize for product direction toward the detection zone, while minimizing the amount of substrate that travels toward the detection zone. This optimization may be carried out by performing control experiments, and/or by calculating the mobilities of the substrate and product under the applied electric field, and applying a bulk flow rate that achieves the desired result.

II. Systems

A. System Elements

Figure 4:
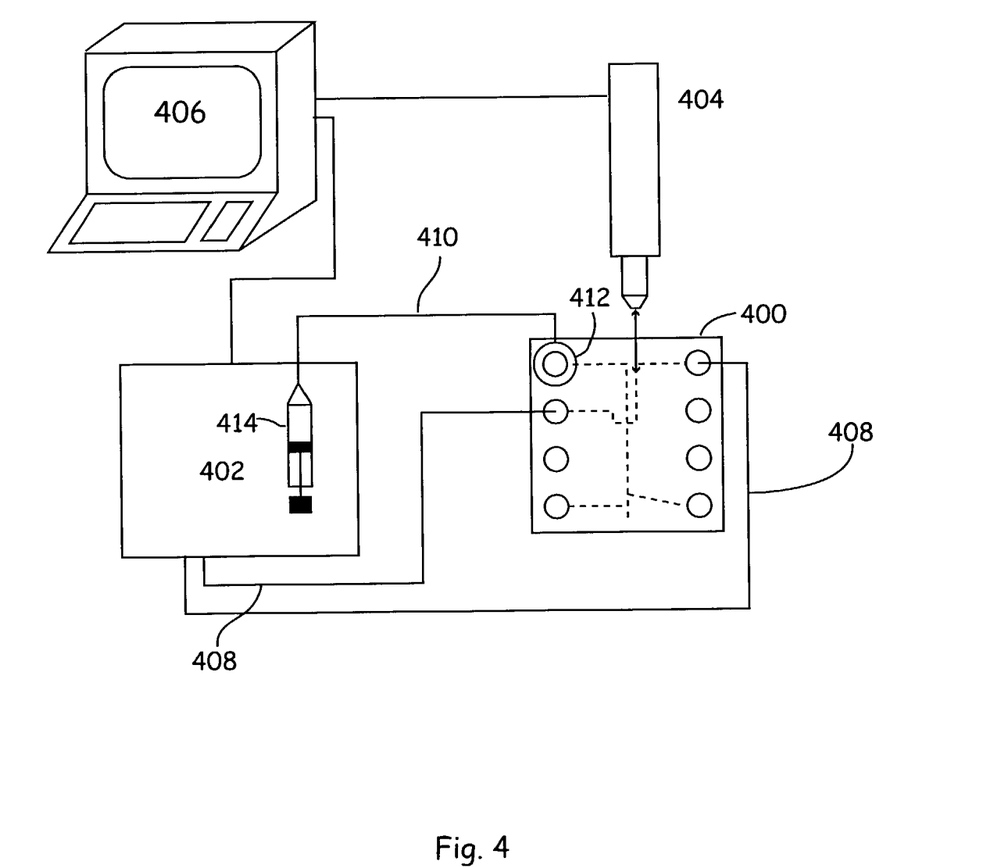
FIG. 4 is a schematic illustration of a microfluidic device and integrated channel network for use in practicing the invention.

In accordance with preferred aspects of the present invention, microfluidic channels or channel networks are operated in conjunction with controller detector systems. In particular, the channel or channel network is typically provided as an integral device that includes one or more channel disposed in a solid body structure. The device is placed into the controller/detector instrument which typically includes a controller for controlling the bulk fluid flow and electric field applied to the channel, as well as a detector for detecting the product in the channel. The overall system is also typically coupled to a computer for recording data from the detector and for instructing the operation of the controller. An example of an overall system for carrying out the present invention is illustrated in FIG. 4. As shown, the system includes a microfluidic device 400 that includes an appropriate channel network disposed therein. The system includes a flow controller 402 that comprises a pressure or vacuum source, e.g., pump 414. The pressure source or pump 414 is shown coupled to one reservoir of the microfluidic device via pressure or vacuum line 410 and vacuum or pressure sealed coupling 412. The controller also includes an electrical power source that is coupled to reservoirs of the microfluidic device via electrodes 408, in order to drive the electrophoretic movement of the assay components. The system also includes a detector 404 as well as a computer or processor 406 that is operably coupled to both the detector 404 and the controller 402. The computer typically includes appropriate programming to receive user input information and transfer that information into instructions for the flow controller. The computer also typically receives the data from the detector and manages that data into a user understandable presentation.

B. Microfluidic Devices

The methods described herein are particularly useful, and gain their greatest flexibility when used in conjunction with integrated microfluidic devices. Microfluidic devices typically comprise a unitary body structure in which is disposed a channel network that includes one or more connected channels, as well as fluid reservoirs for accessing and providing fluid for the various channels of the device to carry out a desired operation. Typically, such devices are fabricated as an aggregate of planar substrate layers, where the channels are fabricated into the surface of one or more of the facing substrates as grooves, wells, or indentations. The mating of one substrate to the other covers the grooves and seals them to form the channels of the device. One or more of the substrates is also provided with apertures disposed through it. These apertures are typically positioned so as to provide access to the channels in the finished device. The apertures also function as the reservoirs of the device for introducing fluids into the channels, as well as providing access for pressure sources and/or electrical connection ports for moving materials through and among the various channels of the device. In certain cases, a sampling element or pipettor is also provided integrated into the body of the microfluidic device. The sampling element typically comprises a capillary that includes a channel or lumen disposed through it. The capillary is attached to the body of the device so as to provide a fluid connection between the capillary lumen and the channel network within the device.

The channels of the device typically include at least one cross-sectional dimension, e.g., width, depth and/or diameter that is within the microscale regime, which as used herein refers to a dimension that is between about 0.1 and 500 μm. In preferred aspects, channels are generally rectangular or trapezoidal in shape and have a depth of from about 2 to about 50 μm, and a width of between about 10 and about 100 μm. Of course, channel dimensions will often vary depending upon the desired application. For example, channels that are intended to conduct particulate containing fluids will typically have larger cross-sectional dimensions to avoid clogging. Similarly, channel cross-sectional dimensions and length are often varied to provide a desired bulk flow characteristic. Specifically, fluidic resistance within channels, and thus, the force required to achieve a particular flow profile are dictated, in part, by the cross-sectional area, as well as the length of the channels that make up the channel network. As such, different flow profiles may include different cross-sectional dimensions.

In addition, the channels of the device may be treated or filled in order to adjust the electrophoretic properties of materials moving through those channels. Treatments include surface treatments, e.g., coatings (static or dynamic), surface derivatization, e.g., silanization and derivatization, etc. Fillings used in adjusting electrophoretic properties include dynamic coating materials such as polydimethylacrylamide polymers that modify the surface properties of the channels, as well as present a sieving matrix for separations.

C. Controllers

The systems of the present invention typically include electrical controllers for driving the electrophoretic movement of materials, as well as controllers for driving bulk flow of fluid through the channels of a microscale fluidic system. Electrical controllers typically include an electrical power supply that is capable of delivering set voltages or currents to or through the channels of the device to drive electrophoresis within those channels. Such power supplies are generally described in, e.g., U.S. Pat. No. 5,800,690, which is incorporated herein by reference in its entirety for all purposes, and include those contained within the Agilent 2100 Bioanalyzer system available commercially from Agilent Technologies, or the Caliper AMS 90 analytical instrument, available from Caliper Technologies Corp. (Mountain View, Calif.).

As noted, the control systems also include an element for controlling bulk flow of fluid within the microscale fluid conduits. Such systems may employ electrokinetic forces, e.g., electroosmotic flow that may be dictated by the applied electric field, as well as the surface properties of the conduit. Such systems are advantageous in that a single control element, namely the electrical controller, is all that is needed to control both electrophoresis and bulk fluid flow.

However, in preferred aspects, a pressure based controller is used to drive bulk fluid flow in the systems of the invention. Such controllers typically include a pressure or vacuum source, e.g., a pump that is coupled to one or more of the ports to the fluid conduit. In the case of microfluidic systems this comprises a pressure or vacuum line from the source or pump, that is coupled to one or more of the reservoirs of the device, and thereby communicates changes in pressure to the channels of the device. In certain cases, multiple pressure sources and connections are used to adjust the pressure at numerous different ports to the device, simultaneously, in order to control precisely the fluid flow through integrated channel networks. Briefly, pressure sources are coupled to the reservoirs at the termini of the channels in an integrated channel network. Examples of such multiple pressure source controllers are described in U.S. application Ser. No. 09/792,435, filed Feb. 22, 2001, which is incorporated herein by reference in its entirety for all purposes. By controlling relative pressures at each of multiple reservoirs, one can precisely control the rate and direction at which fluids move through such integrated channel networks.

The controller systems of the invention typically include a detection system integrated into a single base unit, e.g., such as the Agilent 2100 Bioanalyzer. Such detection systems typically comprise optical detectors, and preferably, fluorescence detectors, again, like the Agilent 2100 Bioanalyzer.

III. Assays

As noted above, the methods and systems of the present invention are particularly useful in carrying out assaying reactions that are characterized by producing a reaction product that has a different electrophoretic mobility from one or more of the reactants or substrates that are combined or reacted to yield that product. Of particular interest are reactions in which differential detection of the product and reactants or substrates is difficult due to the similarity in detectable properties of the two, e.g., inherent optical properties of fluorescent labeling. In one particularly preferred aspect, the present invention is applied to assaying reactions that result in the addition or removal of phosphate groups to or from a particular substrate. These reactions, typically mediated by kinase or phosphatase enzymes, change the nature of the electrical charge on the substrate molecule by adding or removing a highly charged phosphate group to or from the substrate molecule. Typically, assays for these reactions typically include an optically detectable label affixed to the substrate. Without more, both the product and substrate would be indistinguishable, as they would include the same label. However, such assays typically perform a separation function to separate substrate from product, whereupon the product is detected. Such separations include immunoaffinity separations, as well as charge based separations, e.g., chromatographic or electrophoretic. As can be readily appreciated from the instant disclosure, the present invention relies upon the direction of the labeled, e.g., phosphorylated product in the case of a kinase assay, or the unphosphorylated product in the case of a phosphatase assay, toward the detection zone in a microfluidic channel, while the labeled substrate, e.g., a phosphorylated or phosphorylatable substrate for the given assay is directed or at least maintained in a position away from the detection zone.

While phosphatase and kinase assays are particularly benefited by the invention, a large number of other assays can also be performed in the format that is compatible with the invention, or configured to be compatible with that format. By way of example, protease enzyme assays often rely upon the change in size of the labeled substrate, e.g., a large polypeptide, as it is converted to the product, e.g., fragment(s) of the large polypeptide. This change in size is again typically determined by a size-based separation, e.g., using gel exclusion or electrophoretic methods. By configuring a labeled substrate to provide a labeled product that has a different electrophoretic mobility, e.g., changing the charge-to-mass ratio of the product relative to the substrate, one can easily adapt that assay to the format of the invention. For example, one can provide a substrate that has a substantially neutral charge by allocating positively charged groups to one region of the polypeptide, while oppositely charged groups are allocated to another region, where the regions are separated by the putative cleavage point of the enzyme of interest. Cleavage of the large polypeptide (substantially neutral) than yields two fragments that have high net charges, and thus substantially different electrophoretic mobilities.

Similarly, nucleic acid assays may be configured whereupon the reaction yields a product having a different charge:mass ratio from the initial reagent(s). Typically, the charge:mass ratio of naturally occurring nucleic acids is a constant, yielding a constant electrophoretic mobility of all nucleic acids, regardless of size. Electrophoretic separation is generally accomplished by moving the nucleic acids through a sieving matrix which accomplishes the size base separation. In the methods of the present invention, nucleic acid analogs may be employed, e.g., in hybridization probes, so as to significantly change the electrophoretic mobility of, e.g., a hybridized double stranded product relative to a single stranded substrate. In this example, the hybrid would be differentially and preferentially directed toward the detection zone over either a labeled target sequence or labeled probe. For example, uncharged nucleic acid analogs, e.g., peptide nucleic acids, can be used as the probe. Upon hybridization, the mass of the hybridized product is increased relative to single stranded target sequence without any increase in charge. In the case of a labeled target, this allows for differential direction of the hybrid and the single stranded target. Where the probe is labeled, the hybridization reaction suddenly adds substantial charge to the labeled hybrid relative to the labeled probe, again, giving a basis for differentially directing the two in accordance with the invention. A variety of other analogs are also useful in this aspect of the invention, provided the analogs have the ability to yield a shift in the charge to-: mass ratio of the product relative to the labeled substrate. Such analogs include positively charged analogs such as methyl phosphonate polymers and cationic nucleic acid analogs.

IV. Example

Figure 5:
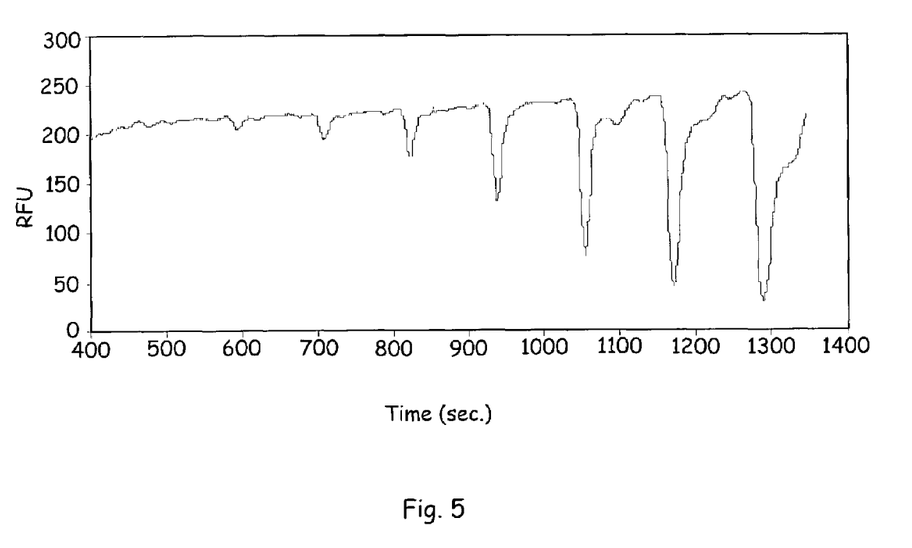
FIG. 5 is a plot of fluorescence from an assay of injected inhibitors using assay formats and methods of the invention.

To illustrate the method, a protein kinase A (PKA) inhibition assay was carried out on an 80A chip, whose schematic layout is shown in FIG. 3A. The peptide substrate for this kinase, FL-LRRASLG-CONH$_2$, was placed in well 320, and the enzyme in well 322. A pressure of −0.5 psi was applied to well 330, while a voltage gradient of 2450V was applied between wells 326 and 328 (2500V to the cathode in well 328, and 50V to the anode in well 326). The continuous pressure-driven flow of substrate and product into the main reaction channel resulted in the conversion of a fraction of the neutral substrate to a negatively charged, phosphorylated product. Under the influence of the applied electric field between wells 326 and 328 this negatively charged product was electrophoretically separated from the neutral substrate, migrated towards well 326 and was detected in the channel leading to this well. The neutral substrate was unaffected by the applied electrical field and migrated toward well 330. In the absence of any PKA inhibitors, a constant fluorescent signal was observed at the detection point. Upon injection of PKI, an inhibitor of protein kinase A, through the capillary attached to the chip, a zone containing a lower concentration of the reaction product was obtained, and this was detected as a temporary decrease of the constant fluorescent signal at the detection point. This decrease of the fluorescent signal was proportional to the concentration of the injected inhibitor, as seen in FIG. 5. Although not shown in this example, the detection point could also be placed in the channel leading to well 330, and in this case the injection of an inhibitor would result in the appearance of peaks of fluorescence intensity instead of dips shown in the example in FIG. 5. The use of a neutral substrate and charged product demonstrates the ability to differentially direct substrate and product in accordance with the methods of the invention, as is indicated by the substantial drop in fluorescent signal in the inhibited regions of the plot of FIG. 5 (e.g., very little neutral substrate was present to produce background fluorescence when the enzyme reaction that yielded fluorescence was inhibited).

All publications and patent applications are herein incorporated by reference to the same extent as if each individual publication or patent application was specifically and individually indicated to be incorporated by reference. Although the present invention has been described in some detail by way of illustration and example for purposes of clarity and understanding, it will be apparent that certain changes and modifications may be practiced within the scope of the appended claims.

What is claimed is:

1. A method of monitoring a reaction, comprising:
   providing a first reaction mixture in a first fluidic conduit, the first reaction mixture comprising:
      a first reagent having a detectable label associated therewith;
      a second reagent that reacts with the first reagent to produce a first product having the detectable label associated therewith, the first product having an electrophoretic mobility that is different from the first reagent;
   providing a detection zone in a second fluidic conduit which is fluidly coupled to the first fluidic conduit at a first intersection,
   directing the first reaction mixture along a length of the first fluidic conduit;
   controllably directing the first product and substantially no first reagent into the second fluidic conduit away from the first intersection; and
   detecting the product at the detection zone in the second fluidic conduit.

2. The method of claim 1, wherein at least 50% of the first reagent is directed away from the second fluidic conduit.

3. The method of claim 1, wherein at least 90% of the first reagent is directed away from the second fluidic conduit.

4. The method of claim 1, wherein at least 95% of the first reagent is directed away from the second fluid conduit.

5. The method of claim 1 wherein the directing the first reaction mixture along a length of the first fluidic conduit comprises applying pressure along the length of the first fluidic conduit.

6. The method of claim 5 wherein said applying pressure is controlled by a pressure controller that is coupled to one or more ports which are fluidly coupled to the first fluidic conduit.

7. The method of claim 6 wherein the first reagent has a non-zero electrophoretic mobility and the pressure in the first fluidic conduit is controlled such that the pressure-based flow of fluid in the first fluidic conduit is of sufficient magnitude to substantially overcome an electrophoretic velocity of the first reagent in the first intersection towards the second fluidic conduit.

8. The method of claim 1 wherein the directing the first reaction mixture along a length of the first fluidic conduit comprises applying an electric field along the length of the first fluidic conduit.

9. The method of claim 8 wherein said applying an electric field is controlled by an electrical controller that is coupled to one or more electrodes which are positioned in one or more respective ports which are fluidly coupled to the first fluidic conduit.

10. The method of claim 1 wherein the first reaction mixture comprises an enzyme, a substrate, and the reaction product of the enzyme and substrate.

11. The method of claim 10 wherein the first reaction mixture further comprises an inhibition agent.

12. The method of claim 1 wherein the first reagent has substantially no electrophoretic mobility.

13. The method of claim 1 wherein the first reagent has an electrophoretic mobility that is in a different direction from the first product.

* * * * *